(12) United States Patent
Bodin et al.

(10) Patent No.: US 7,021,697 B2
(45) Date of Patent: Apr. 4, 2006

(54) VEHICLE AND A VEHICLE DOOR

(75) Inventors: Hans Bodin, Sodra Sunderbyn (SE); Martin Jonsson, Lulea (SE); Jan Krispinsson, Lulea (SE); Lars Wikstrom, Lulea (SE)

(73) Assignee: SSAB Hardtech AB, Lulea (SE)

( * ) Notice: Subject to any disclaimer, the term of this patent is extended or adjusted under 35 U.S.C. 154(b) by 0 days.

(21) Appl. No.: 10/523,041

(22) PCT Filed: Aug. 8, 2003

(86) PCT No.: PCT/SE03/01258

§ 371 (c)(1),
(2), (4) Date: Feb. 2, 2005

(87) PCT Pub. No.: WO2004/014682

PCT Pub. Date: Feb. 19, 2004

(65) Prior Publication Data

US 2005/0253415 A1    Nov. 17, 2005

(30) Foreign Application Priority Data

Aug. 8, 2002  (SE) .................................... 0202381

(51) Int. Cl.
*B60J 5/04* (2006.01)
(52) U.S. Cl. ................................ 296/146.6; 296/146.9; 296/187.12

(58) Field of Classification Search ............ 296/146.9, 296/146.5, 146.6, 187.12; 49/502, 503
See application file for complete search history.

(56) References Cited

U.S. PATENT DOCUMENTS

| 3,819,228 A   | 6/1974 | Cornacchia |
| 5,306,067 A * | 4/1994 | Hull et al. ................ 296/146.6 |
| 5,518,290 A * | 5/1996 | Reinhard et al. ........ 296/146.6 |

FOREIGN PATENT DOCUMENTS

| DE | 10128864 | 12/2002 |
| SE | 518503 | 10/2002 |
| WO | 03059667 | 7/2003 |

* cited by examiner

Primary Examiner—Joseph D. Pape
(74) Attorney, Agent, or Firm—Mark P. Stone

(57) ABSTRACT

A vehicle door has a supporting frame (10) substantially in the form of a rectangular annular hat beam (13–16) of high-strength steel, which, with its outer side flange (17), carries the outer panel (28) of the door and has its crown (12) towards the vehicle interior. The lower rear portion of the outer side flange (17) has a bolt 32 arranged to fit in a hole (35) in the pillar (34). In case of a side impact, the bolt will make the pillar participate in the energy absorption. The frame (10) is comparatively shallow and it can therefore have a high yield strength and all the other elements of the door can be mounted on the inside of the frame, which make them easily available for service.

20 Claims, 6 Drawing Sheets

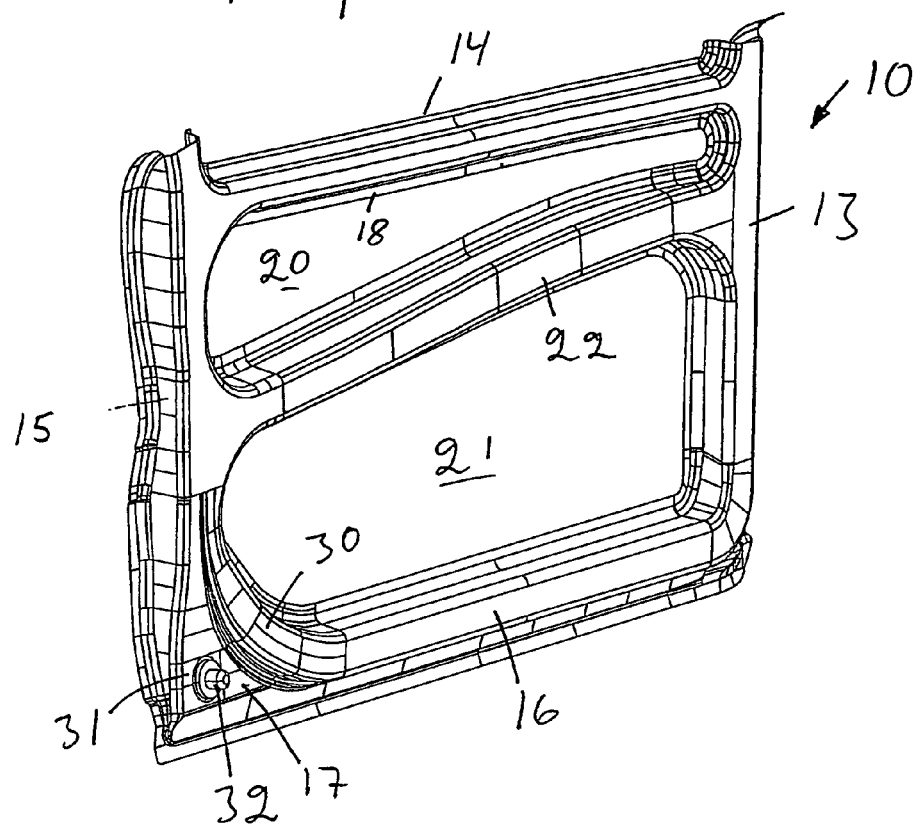
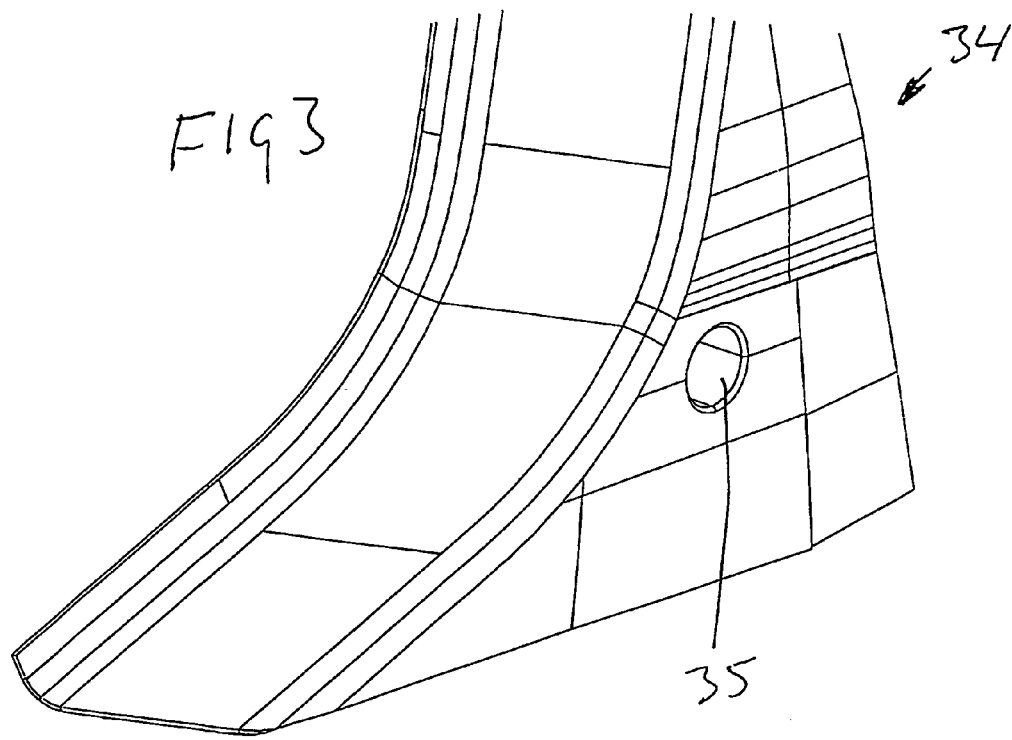

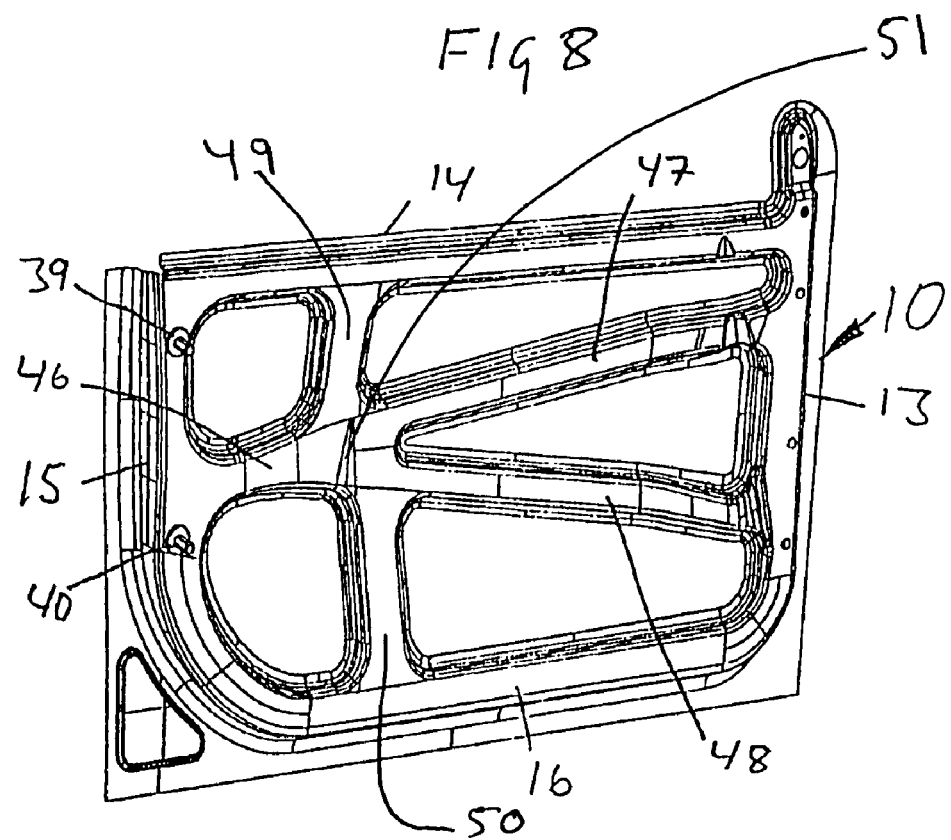
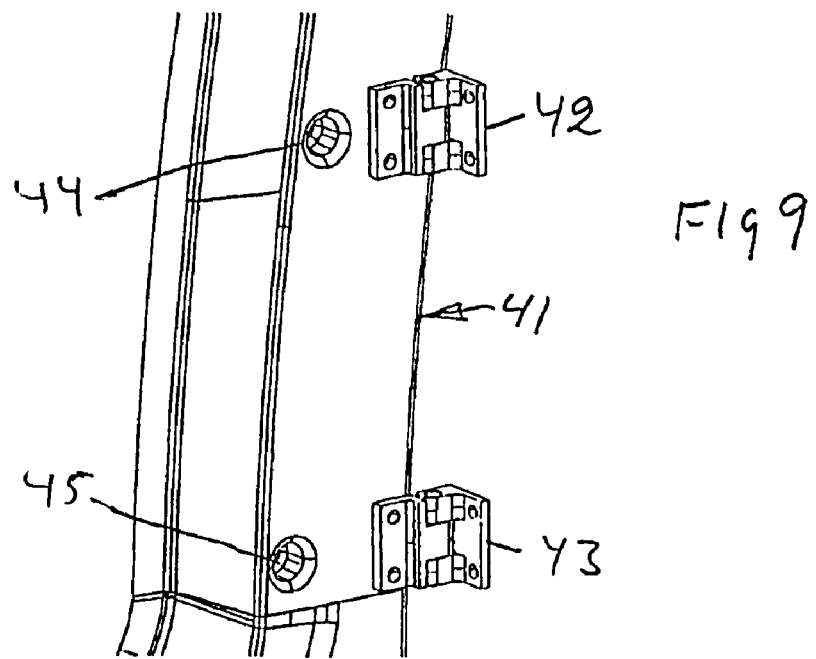

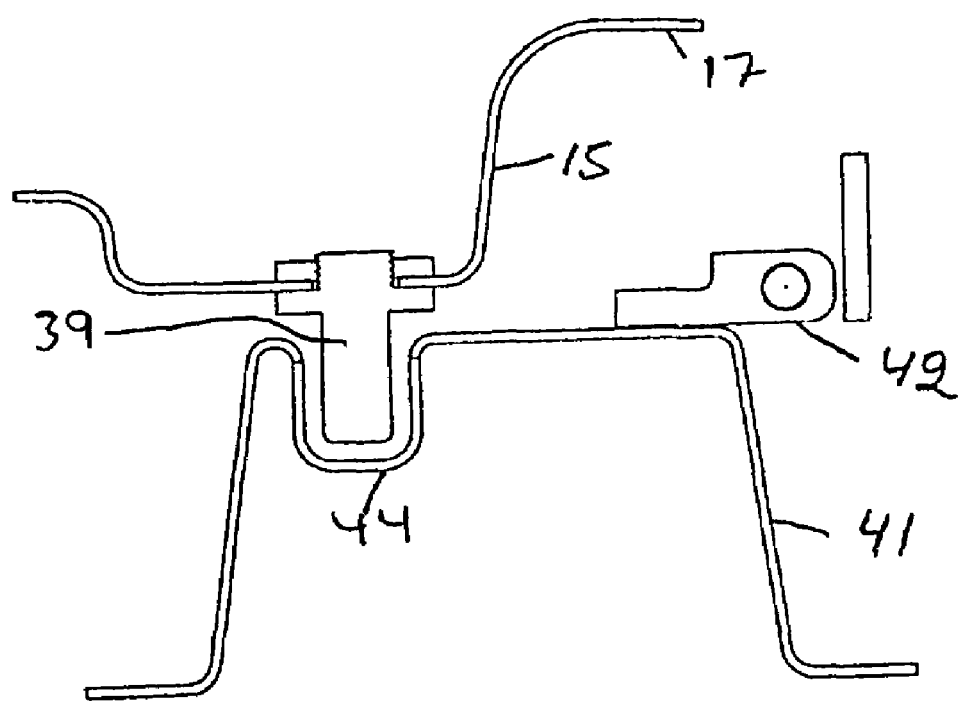

VEHICLE AND A VEHICLE DOOR

TECHNICAL FIELD OF THE INVENTION

This invention relates to a vehicle having a door and to a vehicle door.

TECHNICAL BACKGROUND OF THE INVENTION AND BRIEF DESCRIPTION OF THE INVENTION

Modern vehicle doors usually consist of a supporting deep drawn so called inner panel that comprises the entire thickness of the door. An outer panel is bent around the edges of the inner panel and secured with cement in its bends. The inner panel is deep drawn and it can therefore not be formed from high-strength steel. A so called waist rail under the window is welded to the inner panel and it can be located inside of or outside of the window. A side impact guard beam of steel with considerably higher strength than the inner panel is also welded to the inner panel and located adjacent the outer panel. A relatively flat trim is fastened on the inner panel. The interior elements of the door such as window guides and window lifts are located inside the deep inner panel. The end sides of the door consist completely of the end sides of the inner panel and the side of the inner panel adjacent the vehicle interior has only comparatively small openings, which makes the mounting of the inner elements of the door difficult.

In prior art, it is known to fasten a hook on the side impact guard beam and have this hook extending out through the rear end side of the inner panel for engagement with a dent on the pillar. Then, the pillar will participate in the energy absorption when the side impact guard beam will be bent inwardly when the door is impacted upon.

OBJECT OF INVENTION AND BRIEF DESCRIPTION OF THE INVENTION

It is an object of the invention to provide a vehicle door that is lighter in weight and stronger than conventional doors and provides an improved protection, when impacted upon, by providing means that engages with the pillar of the vehicle on which the door is mounted. Said means should not be an obstacle for the passengers when they enter the vehicle or move out of it. The invention also relates to a vehicle having such a door.

This is fulfilled principally in that the door has a supporting frame substantially in the form of a rectangular annular hat beam of high-strength steel, which, with its outer side flange, carries the outer panel of the door and has its crown towards the vehicle interior, the rear portion of the hat beam having a bolt arranged to fit into a hole in the pillar.

The bolt can suitably have a thread and be fastened with a nut on the outer side of the flange.

The frame can suitably have a side impact guard beam between the two standing portions of the annular hat beam, and the side impact guard beam can suitably be formed, as an integral part of the door frame, from the same sheet blank as the door frame. The side impact guard beam can be a hat beam too.

A deep inner panel is suitably mounted on the supporting frame of the door and does not cover the step with the bolt but covers the interior elements of the door, such as for example the window structure, which are located between the inner panel and the supporting frame of the door. Suitably, the inner panel and the supporting frame form together the end side of the door, and the inner panel may constitute the major portion of the width of the end side.

The invention is defined by the claims.

BRIEF DESCRIPTION OF THE DRAWINGS, WHICH ILLUSTRATE A PREFERRED EMBODIMENT

FIG. 1 is a perspective view of a frame of a door seen obliquely from behind/inside.

FIG. 3 shows in a perspective view the lower portion of a pillar.

FIG. 8 is a modified design of the frame shown in FIG. 1 seen from inside the vehicle.

FIG. 9 shows, seen from outside, a portion of the B-pillar at the rear of the door shown in FIG. 8.

FIG. 10 is a fragmentary section through a portion of the door and the B-pillar shown in FIGS. 8 and 9.

DESCRIPTION IN MORE DETAIL OF THE ILLUSTRATED EMBODIMENT

Figure 2:
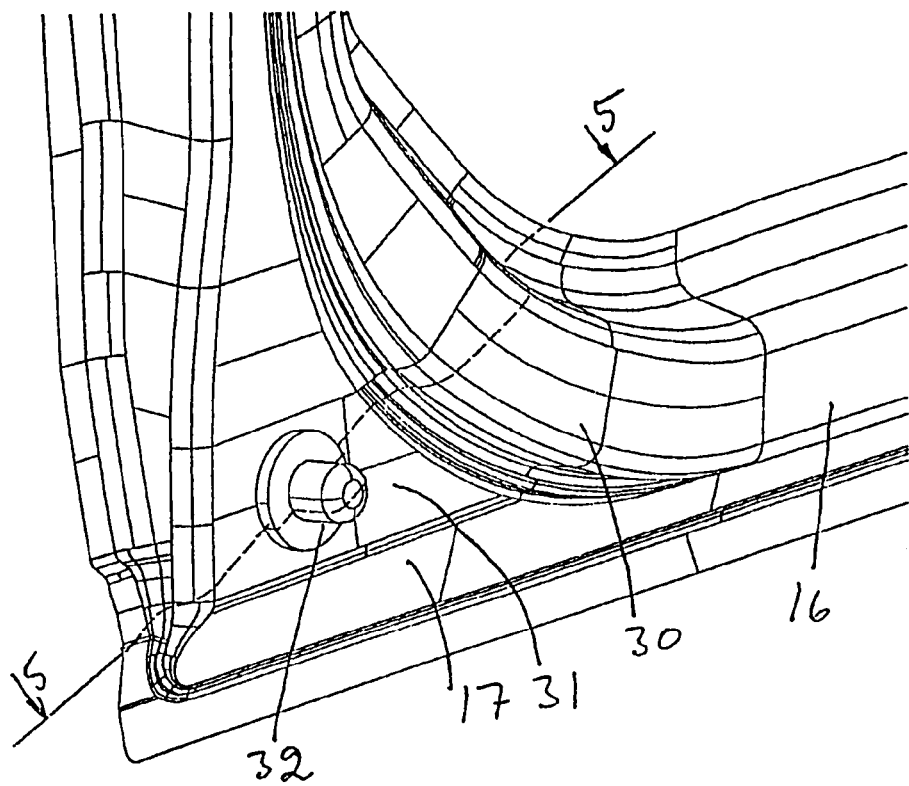
FIG. 2 is an enlarged view of one corner of the frame shown in FIG. 1.

FIG. 1 shows a frame 10 of the left front door of a vehicle, and the frame is seen from inside the vehicle and obliquely from behind. The frame is formed from a flat sheet so that it has got an annular hat beam 13-16 with a crown 12, side flanges 17,18 and intermediate webs 11,19 as best can be seen from FIG. 4. The outer side flanges 17 have a varying width so that they adapt to the outer panel of the door. The hat beam has its crown towards the vehicle interior. The hat beam has four straight portions 13,14,15,16 interconnected by bends. A hole 20,21 is formed in the middle of the annular hat beam and a side impact guard beam 22 extends between the upstanding beam portions 13 and 15 and bridges the hole 20,21. The beam 22, too, can have an open hat profile with its crown inwards as shown but it may also have a cover fastened by spot welding. It may also have another cross section and it may for example have a double hat profile and have its open side towards the vehicle interior. Various portions of the hat beam 13-16 may have various profile and some portions may for example be a double hat.

Figure 5:
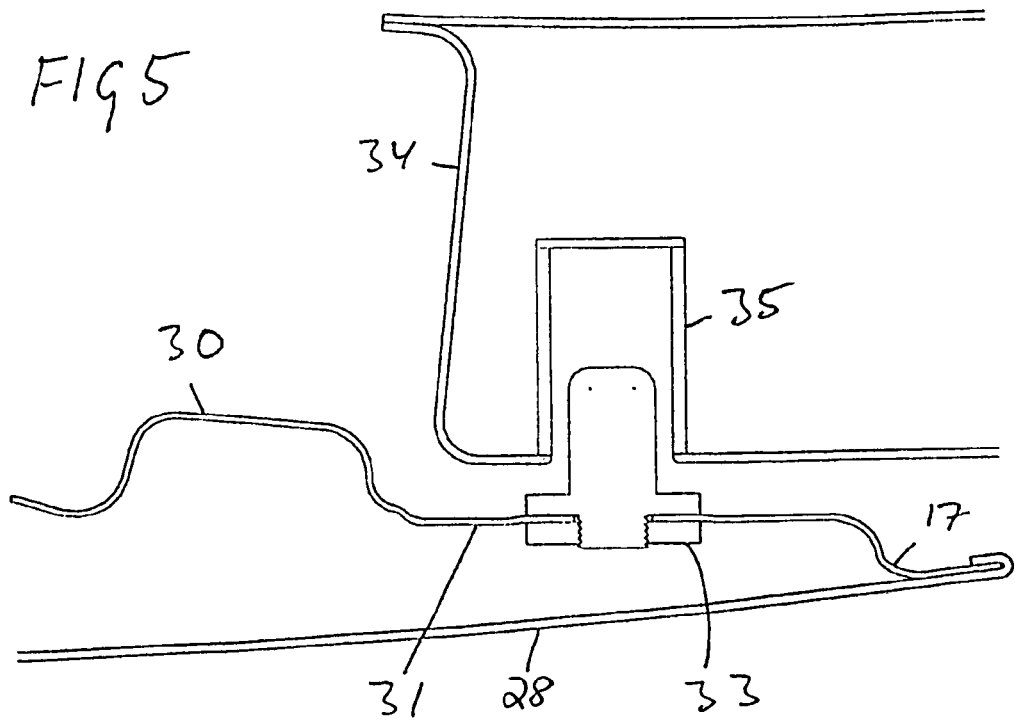
FIG. 5 is a section taken as indicated by the arrows 5—5 in FIG. 2.
Figure 4:
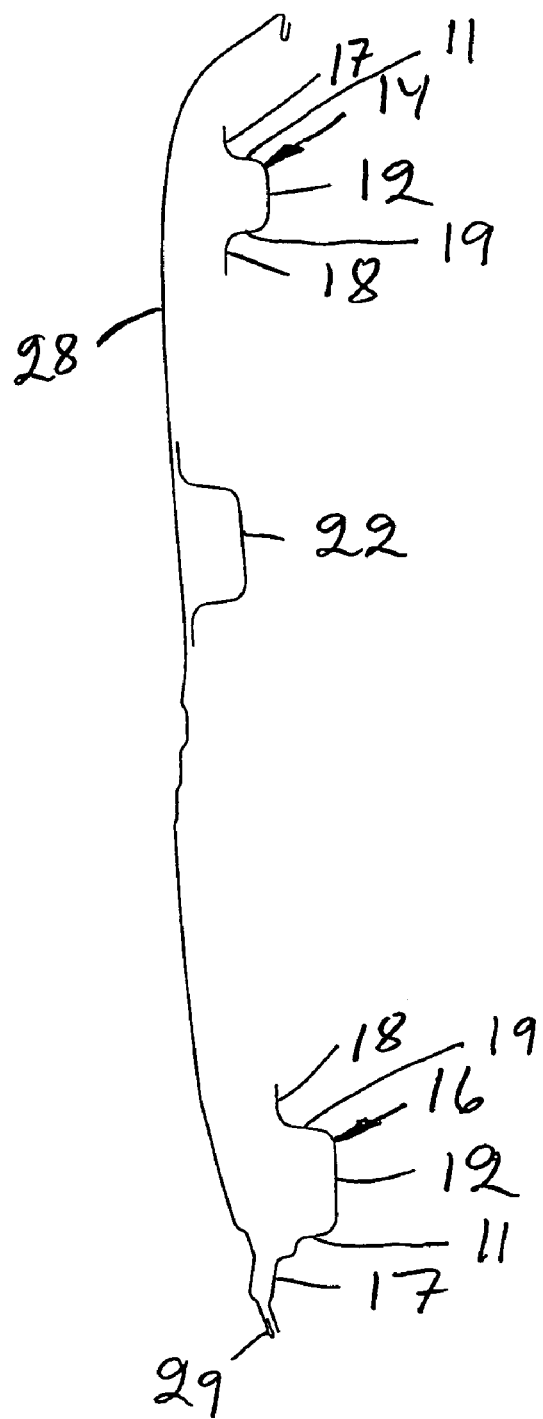
FIG. 4 is a vertical section through the frame and an outer panel.

An outer panel 28 of sheet metal is shown in the FIGS. 4 and 5. It is bent around the outer flange 17 of the hat beam portions 13,15,16 and it can have cement in the bends or it can be fastened in another way, for example by laser welding. In FIG. 4, the bend 29 is shown but, for clarity, it is shown separate and not bent around the side flange 17. The side impact guard beam 22, as well as all the other portions of the frame will be close to the outer panel, that is, the impact guard will be as far out from the passenger as possible, which is advantageous. In its rear lower portion, the hat beam has a long bend 30 between the horizontal hat beam portion 16 and the standing hat beam portion 15 so that the outer side flange 17 is wide there. It rises continuously towards the crown of the standing hat beam portion 16 and its lower portion forms a step 31 as can be seen from FIG.

1 and FIG. 5. Higher up towards the standing hat beam 15, the step 31 can instead be regarded as a step on the web 11 of the hat beam. A bolt 32 is fastened in the lower portion of the step 31 by extending through a hole in the step and having a nut 33 at the back, that is, adjacent the outer panel 28. The nut has enough space between the step and the outer panel 28, and the bolt is mounted before the outer panel is fastened to the frame.

In FIG. 5, the lower part of the pillar 34 at the rear of the door is shown, that is, the B-pillar in the illustrated example when the door is a front door. The pillar in which the hinges of the door are fastened is called the A-pillar. If the door instead is a rear door, it is hinged in the B-pillar and has its lock and the bolt 32 against the C-pillar. The lower portion of the B-pillar is separately shown in FIG. 3. The lower and illustrated portion of the pillar is welded to the non-illustrated side rail of the vehicle and it is widened as a bow forwards toward the connection. The bend 30 of the hat beam is adapted to this bow of the pillar. As seen along the vehicle, the bend and the bow overlap partly so that the frame 10 of the door can transmit force from the A-pillar to the B-pillar when there is a frontal crash.

The pillar 34 has a hole in which a steel sleeve 35 with a bottom is welded so that the closed pillar will not have an open hole. As shown in FIG. 5, the bolt 32 enters the sleeve 35 when the door is closed and it is a large space between the sleeve and the bolt. In case of a side impact on the door, the frame of the door and the side impact guard beam 33 will be deformed inwards. At its front end, the frame is rigidly fastened in the hinges but at its rear end, it is fastened only by the comparatively weak lock. In the deformation, the rear end of the frame 10 will be drawn forwards and the bolt 32 will then engage with the sleeve of the pillar and thereby will the pillar participate in the energy absorption. The sleeve may alternatively be a plastic sleeve that is inserted in the hole of the pillar provided that the edge of the hole is reinforced, but a steel sleeve welded to the pillar is preferred because it will provide for a stronger coupling between the frame of the door and the pillar.

Figure 6:
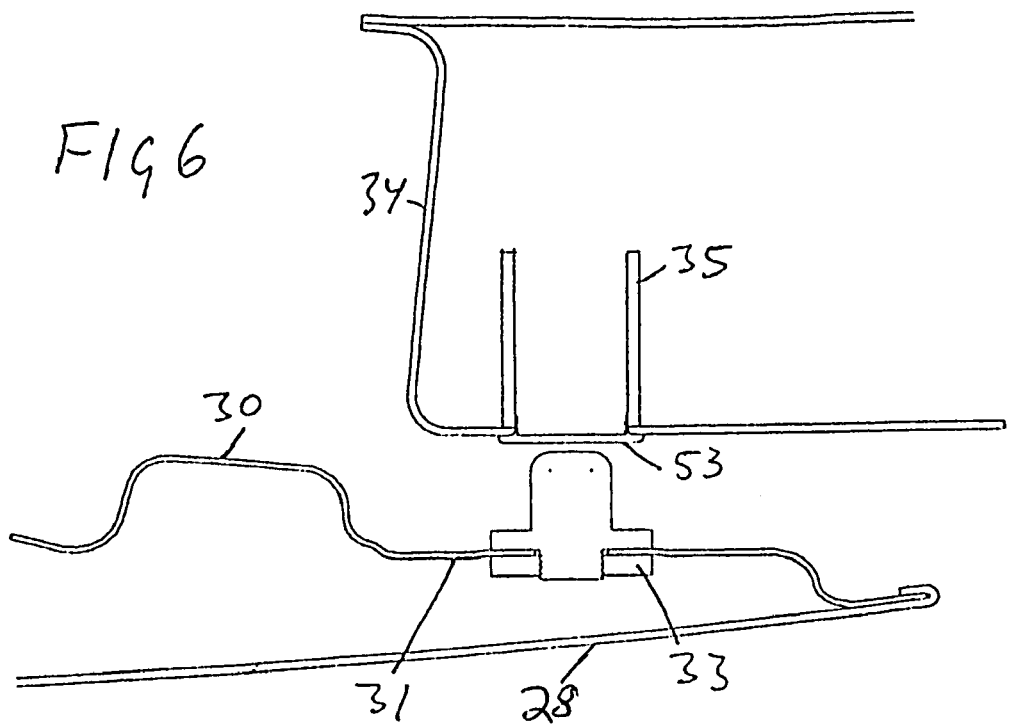
FIG. 6 is a section corresponding to FIG. 5, but showing a somewhat modified design.

FIG. 6 show a modified design in which the steel sleeve 35 does not have a bottom but instead a plastic cover 53. As does FIG. 5, this figure shows the door in closed position and in this case, the bolt does not enter the sleeve 35 until the door has been deformed inwardly. The design according to FIG. 5 is preferred. If the edge of the hole is reinforced, the steel sleeve can be dispensed with and a cover can cover the hole directly.

Figure 7:
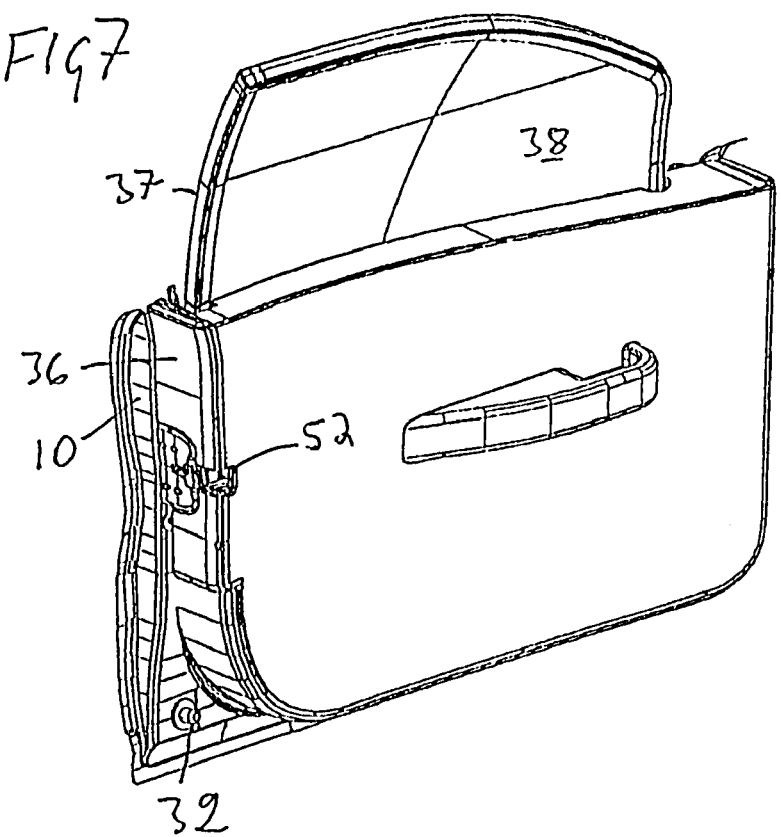
FIG. 7 is a perspective view of a complete door built on the frame shown in FIG. 1.

FIG. 7 shows an assembled door. An inner panel 36 is mounted on the frame 10 and between the frame and the inner panel is mounted a window structure with a protruding window frame. The holder for the rear view mirror is not illustrated in the figures but it can suitably be an integrated part of the frame 10. The inner panel 36 has end sides and a bottom, which connect to the hat beam of the frame, and the frame and the inner panel thus form together the end sides and the bottom of the door. The inner panel has also an upper side that connects to the window 38. Suitably, all the interior elements of the door such as the lock 52, that co-acts with a non-illustrated means on the pillar, and the window structure 37 will be pre-mounted on a frame to form a unit that also may comprise the inner panel 36. The entire unit can be mounted on the frame 30 by screws through the inner panel. Thus, the inner panel need not be supporting but may be made of plastics and be covered by a snap-on trim that covers the screws. The inner panel 36 may be deep and present a large portion of the thickness of the door instead of the supporting portion of the door comprising practically the entire door thickness. The inner panel is thus deep as compared to the frame of the door.

In this way, one will achieve a very high strength of the supporting frame 10 of the door. Its thickness can be less than half the thickness of the door. The forming of the frame will be facilitated by the frame being thin in comparison with the entire door thickness and a frame can therefore be made that has steel of very high strength. In a conventional door that has a deeper forming of its supporting part, one must use steel with lower strength.

Suitably, the frame 10 of the door is formed in the press hardening method, that is, a blanket of hardenable flat steel sheet is hot stamped to form the supporting frame with its integrated side impact guard beam and the thus formed frame is hardened while remaining in the forming tools. Then, when assembling the door, one attaches the outer panel to the supporting frame.

Since the frame 10 of the door can be made comparatively thin, it can alternatively be made of high-strength cold forming steel, but it will then not be possible to reach as high strength as in press hardening. With the latter method, a yield strength of over 1000 N/mm$^2$ can be reached or at least 800 N/mm$^2$, somewhat depending on the thickness of the frame. The elongation to rupture will also be smaller by the cold forming than by the hot stamping. A vehicle door according to the invention is, however, advantageous also if it has comparatively low strength steel, for example a yield strength of 350 N/mm$^2$. However, a cold forming steel with a yield strength of 500 N/mm$^2$ or higher can probably be used.

Besides giving a door that is lighter in weight and faster to assembly at the first assembly, the design of the illustrated door will provide for simpler demount and remount for service. All the elements of the door will be available since they are all located on the inside of the supporting frame.

FIGS. 8–10 show a design of a frame 10 of a front door, a left hand door, that has two bolts 39,40 at the rear vertical portion 15 of the frame of the door. The pillar 41, the B-pillar, at the back of the front door has two hinges 42,43 for fastening the rear door, and the B-pillar has holes in the form of sleeves 44,45 for receiving the bolts 39,40 in the way described with reference to FIGS. 1–7. These sleeves are located ahead of the hinges. In the conventional way, the B-pillar can be reinforced by reinforcing plates at its inside at the mountings for the hinges, and it is advantageous that the bolts engage where the B-pillar is reinforced. Such reinforcement, however, is not illustrated in FIG. 10. As in FIG. 1, the side impact guard of the frame 10 has a horizontal beam 46. This beam is in this design bifurcated into two portions 47,48 and it has vertical supports 49,50 to the horizontal portions 14 and 16 of the hat beam so that five holes are formed in the frame 10. All these portions 46–50 of the side impact guard are hat beams and a flat 51 is formed where these hat beams meet. It can also be considered that the side impact guard comprises a beam between the horizontal portions of the frame and a beam between the vertical portions of the frame and that these beams intersect.

The invention claimed is:
1. A vehicle with a door, said vehicle characterised in that:
said door comprises a supporting frame substantially in the form of a rectangular annular hat beam of high-strength steel, said hat beam having an outer side flange for carrying an outer panel of the door, and a crown facing towards the vehicle interior, a rear portion of the hat beam having a bolt arranged to fit into a hole in a pillar of said vehicle.

2. A vehicle according to claim 1, characterised in that the bolt is arranged on a lower, rear portion of the outer side flange of the hat beam.

3. A vehicle according to claim 2, characterised in that said hole is disposed on a lower portion of the pillar, said lower portion of said pillar being widened in a bow form forwards in a direction towards a region at which said pillar is joined with a side rail of the vehicle, and a lower rear bend of the hat beam is adapted to the widened portion of the pillar so that the outer side flange is widened to cover the widened portion of the pillar for carrying the bolt on said widened portion of said outer side flange.

4. A vehicle according to claim 1, characterised in that the bolt has a thread and is secured by a nut at the outer side flange, the bolt being located on a step on the outer side flange so as to provide a space for the nut between the outer side flange and the outer panel of the door.

5. A vehicle according to claim 1, characterised in that the door is a front door and the pillar is a B-pillar with hinges for a rear door, said pillar having a hole for a bolt adjacent each said hinge, the rear portion of the supporting frame having bolts adapted to fit into said holes.

6. A vehicle according to claim 1, characterised by a side impact guard disposed between two standing portions of the hat beam.

7. A vehicle according to claim 6, characterised in that the side impact guard is formed, as an integral part of the supporting frame, from the same sheet blank as the supporting frame.

8. A vehicle according to claim 7, characterised in that the side impact guard comprises a hat beam.

9. A vehicle according to claim 7, characterised in that the side impact guard comprises a beam between vertical portions of the supporting frame and a beam between horizontal portions of the supporting frame.

10. A vehicle according to claim 4, characterised in that a deep inner panel is mounted on the supporting frame of the door and does not cover the step with the bolt, said inner panel covering interior elements of the door, including window structure, placed between the inner panel and the supporting frame.

11. A vehicle door characterised in that said door comprises a supporting frame substantially in the form of a rectangular annular hat beam of high-strength steel, said hat beam having an outer side flange for carrying an outer panel of the door, and a crown facing towards the vehicle interior, a rear portion of the hat beam having a bolt arranged to co-act with a pillar.

12. A vehicle door according to claim 11, characterised by a side impact guard formed, as an integral part of the supporting frame, from the same sheet blank as the supporting frame, said side impact guard extending between two standing portions of the hat beam.

13. A vehicle door according to claim 12, characterised in that the side impact guard comprises a hat beam.

14. A vehicle door to according to claim 12, characterised in that the side impact guard comprises a beam between vertical portions of the supporting frame and a beam between horizontal portions of the supporting frame.

15. A vehicle door according to claim 11, characterised in that an inner panel, mounted on the supporting frame, is deep relative to the supporting frame and does not cover the part of the outer side flange of the hat beam carrying the bolt, said inner panel covering interior elements of the door, including window structure, located between the inner panel and the supporting frame.

16. A vehicle door according to claim 11, characterised in that the steel of the supporting frame has a yield strength of at least 800 N/mm$^2$.

17. A vehicle according to claim 2, characterised in that the bolt has a thread and is secured by a nut at the outer side flange, the bolt being located on a step on the outer side flange so as to provide a space for the nut between the outer side flange and the outer panel of the door.

18. A vehicle according to claim 8, characterised in that the side impact guard comprises a beam between vertical portions of the supporting frame and a beam between horizontal portions of the supporting frame.

19. A vehicle door to according to claim 13, characterised in that the side impact guard comprises a beam between vertical portions of the supporting frame and a beam between horizontal portions of the supporting frame.

20. A vehicle door according to claim 12, characterised in that an inner panel, mounted on the supporting frame, is deep relative to the frame and does not cover the part of the outer side flange of the hat beam carrying the bolt, said inner panel covering interior elements of the door, including window structure, located between the inner panel and the supporting frame.

* * * * *